United States Patent [19]
Specht et al.

[11] Patent Number: 5,528,320
[45] Date of Patent: Jun. 18, 1996

[54] PROTECTIVE EYEWEAR

[75] Inventors: Paul B. Specht, Wilmette, Ill.; Woodie M. Zachry, Jr., Spring, Tex.

[73] Assignee: Encon Safety Products, Houston, Tex.

[21] Appl. No.: 437,551

[22] Filed: May 9, 1995

[51] Int. Cl.$^6$ .............................. G02C 1/04; G02C 5/20
[52] U.S. Cl. ................. 351/106; 351/92; 351/118; 351/121; 16/228
[58] Field of Search ..................... 351/86, 89, 91, 351/92, 93, 96, 105, 106, 109, 44, 164, 111, 118, 121, 113, 114; 2/13, 441; 16/228

[56] References Cited

U.S. PATENT DOCUMENTS

| | | | |
|---|---|---|---|
| D. 141,029 | 4/1945 | Splaine | D16/314 |
| D. 182,463 | 4/1958 | Gay, Jr. et al. | D16/314 |
| D. 321,703 | 11/1991 | Grau | D16/314 |
| D. 337,596 | 7/1993 | Canavan | D16/123 |
| D. 356,322 | 3/1995 | Bolle | D16/314 |
| 3,441,975 | 5/1969 | Sheperd | 16/150 |
| 3,667,834 | 6/1972 | Davison et al. | 351/118 |
| 3,713,732 | 1/1973 | Gooch | 351/153 |
| 4,153,348 | 5/1979 | Walters et al. | 351/118 |
| 4,271,538 | 6/1981 | Montesi et al. | 2/439 |
| 4,850,058 | 7/1989 | Cheng | 2/448 |
| 4,878,749 | 11/1989 | McGee | 351/158 X |
| 4,955,708 | 9/1990 | Kahaney | 351/44 |
| 5,000,558 | 3/1991 | Blackstone | 351/111 |
| 5,059,017 | 10/1991 | Bennato | 351/121 |
| 5,170,502 | 12/1992 | Hengendörfer | 2/13 |
| 5,257,050 | 10/1993 | Wiedner | 351/86 |
| 5,357,292 | 10/1994 | Wiedner | 351/105 |
| 5,379,463 | 1/1995 | Schleger et al. | 2/447 |
| 5,381,192 | 1/1995 | Canavan et al. | 351/118 |
| 5,386,254 | 1/1995 | Kahaney | 351/153 X |
| 5,423,092 | 6/1995 | Kawai | 351/44 |

*Primary Examiner*—William L. Sikes
*Assistant Examiner*—Huy Mai
*Attorney, Agent, or Firm*—Jenkens & Gilchrist

[57] ABSTRACT

The present application describes protective eyewear having a unitary brow bar with temples and flexible molded hinges. The temples may be adjusted in length. The frame includes integrally molded flexible hinges which allow the temples to collapse. A unitary spherical lens is selectively attached to the frame and can be adapted to wrap around the forehead of the wearer's temples and include a nose bridge for supporting the lens on the wearer's nose. A stabilizing strip may be used to hold the frame and lens in place when the eyewear is assembled.

6 Claims, 3 Drawing Sheets

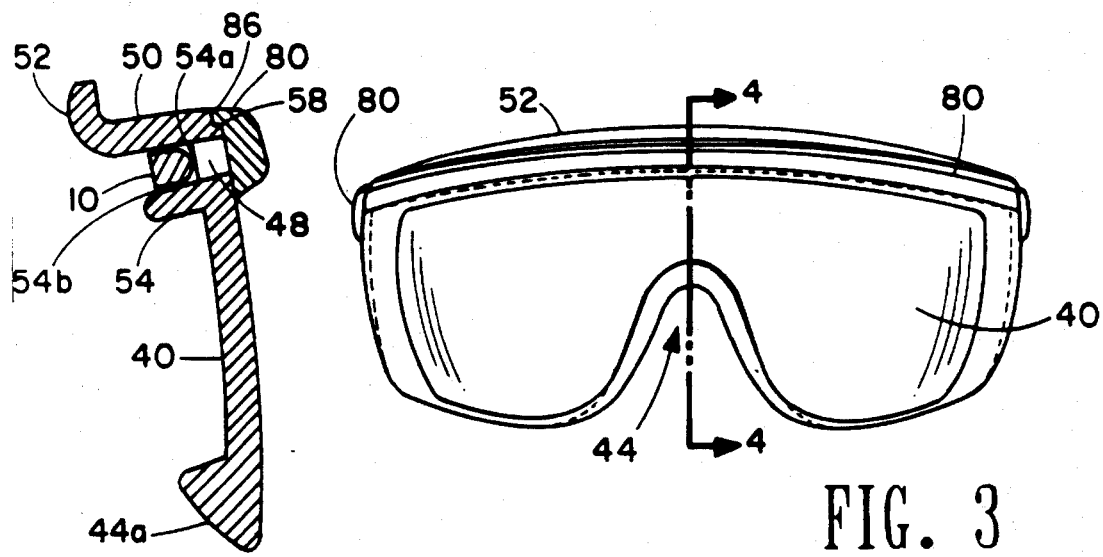
FIG. 4
FIG. 3
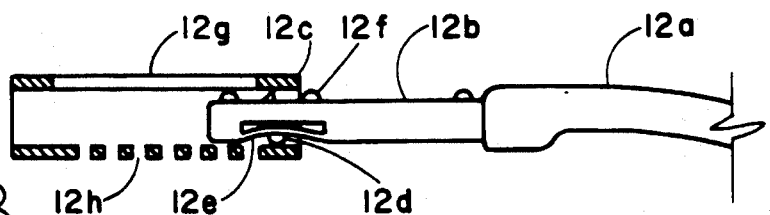
FIG. 2B
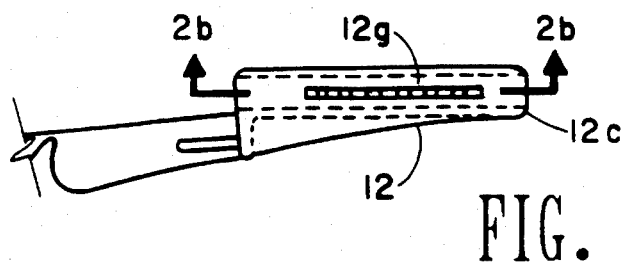
FIG. 2A

PROTECTIVE EYEWEAR

BACKGROUND OF INVENTION

1. Field of the Invention

The present invention generally relates to protective eyewear, and more particularly to inexpensive protective eyewear having a brow bar molded with a flexible hinge to a temple piece and a unitary lens attachable for easy assembly by the purchaser without tools to the brow bar.

2. Description of Related Art

Most eyeglasses or spectacles manufactured today include a lens supporting structure or frame to which temples are pivotally attached by means of a hinge assembly. The hinge assembly can be metal or plastic and typically comprises interleaved hinge plates with aligned apertures. The hinge plates are attached respectively to the frame and the temple of the spectacles. A vertically disposed hinge pin or screw passes through the interleaved apertures and secures the hinge plates of the frame to the hinge plates of the temple. Spectacles of this construction are inappropriate for assembly by a purchaser resulting in many independent process steps in the manufacture and assembly. For the purchaser to assemble safety spectacles for immediate use in hazardous areas on plant properties, or for use as sunglasses, it is necessary that it be possible without the need for assembly tools. This requirement forces the construction of the entire spectacle from a material which can be easily handled by hand; i.e., a plastic forming the brow and temples area of the spectacles and easily, yet securely, fastening to the lens of the spectacles.

When the spectacles are worn, the frame is supported on the nose of the wearer by a bridge piece, the lens or lenses are located in front of the eyes, and the temples extend rearwardly along the sides of the heads and may engage, with ear pieces, behind the ears of the wearer. For conventional spectacles, synthetic resin materials may be used or other materials such as wires and metals can be employed in whole or in part.

Resilient hinges, which allow the temples to open to a plane beyond their normal use, are well known and have been applied to spectacles as described in U.S. Pat. No. 5,059,017 and more particularly, in U.S. Pat. No. 3,713,732 which shows a flexible hinge integrally molded into a brow piece of a two-piece spectacles. More recently, U.S. Pat. No. 5,059,017 discloses an elastically compressible bellows-like hinge that can be temporarily coupled to the frame and temple. While the spectacle hinge assemblies described above may provide for some advantages, prior art attempts to produce a safety spectacle which is inexpensive, yet easy for the consumer to assemble into a secure eyewear, until now, was still wanting.

The prior art also discloses many transparent plastic safety spectacles or goggles having a single face piece or front protective member hinged to one piece pivotal plastic temples. For example, U.S. Pat. No. 4,271,538 discloses safety spectacles having a one piece ranged and curved front face piece adapted to wrap around the forehead to the wearers temples. However, these spectacles are formed by assembly of several independently manufactured pieces and do not lend to self-assembly. Unfortunately, when the face piece is scratched or becomes cracked, there is no practical alternative to discarding the entire spectacle and replacing it with a new one. Furthermore, the presently available eyewear, particularly low-cost protective spectacles provide mostly flat lens or curved lens in only a single plane. There exists an unsolved need for protective eyewear in which a unitary lens, particularly a spherical lens, may be easily assembled for use on the spot without the need for external tools, thus, scratched lens may be replaced with a new one or a tinted lens for functional or cosmetic reasons.

Still needed is a new two piece, easily assembled pair of glasses which are also easily molded and manufactured. The spectacles of the invention provide that advantage.

SUMMARY OF INVENTION

The present invention relates to protective eyewear having a unitary brow bar molded to connect with temples through formed flexible hinges which allow the temples to pivot between an opened and collapsed position. Preferably, the temples may be adjusted in length. The spectacles of the invention are specifically created to allow easy assembly by the wearer without the use of tools. To accomplish this result, a unitary lens is selectively attached to the brow bar by a simple combination of tabs and slots and preferably is adapted to wrap around the forehead to the wearer's temples and include a nose bridge, normally molded for additional comfort, for supporting the lens on the wearer's nose. A generally cosmetic stabilizer strip may be placed along the top of the lens to improve aesthetic acceptance of the spectacles and to stabilize the frame and lens in place when the eyewear is assembled. The strip is attached to the lens over tabs in the front face of the lens along the top and secured on the ends with hooks which grasp corresponding notches on the lens.

The temple pieces and the brow bar are molded together in a single piece joined together through the flexible hinge strips, sometimes called a "living hinge". Preferably, the temples are made in two pieces which allow them to be adjusted to fit the head of the wearer by telescoping a post on the rear portion into a sleeve on the front portion which is attached to the brow bar through the hinge.

BRIEF DESCRIPTION OF THE DRAWINGS

The accompanying drawings, which are incorporated in, and form a part of, the specification, illustrate the embodiments of the present invention, and, together with the description, serve to explain the principles of the invention. In the drawings:

FIG. 2a shows the detail from the top of the extensible temples of the embodiment of the present invention where the temple pieces are adjustable.

FIG. 2b shows a section of the receptacle of the adjustable temple with the rear portion inserted.

FIG. 3 is a front elevation of the assembled frame, lens, and strip shown in FIG. 1. assembly of the lens to the frame.

FIG. 4 is a section view of the assembled spectacles along line 4—4 of FIG. 3.

It is to be noted that the drawings illustrate only typical embodiments of the invention and are therefore not to be considered limiting of its scope, for the invention will admit to other equally effective embodiments.

DETAILED DESCRIPTION OF THE INVENTION

Figure 1:
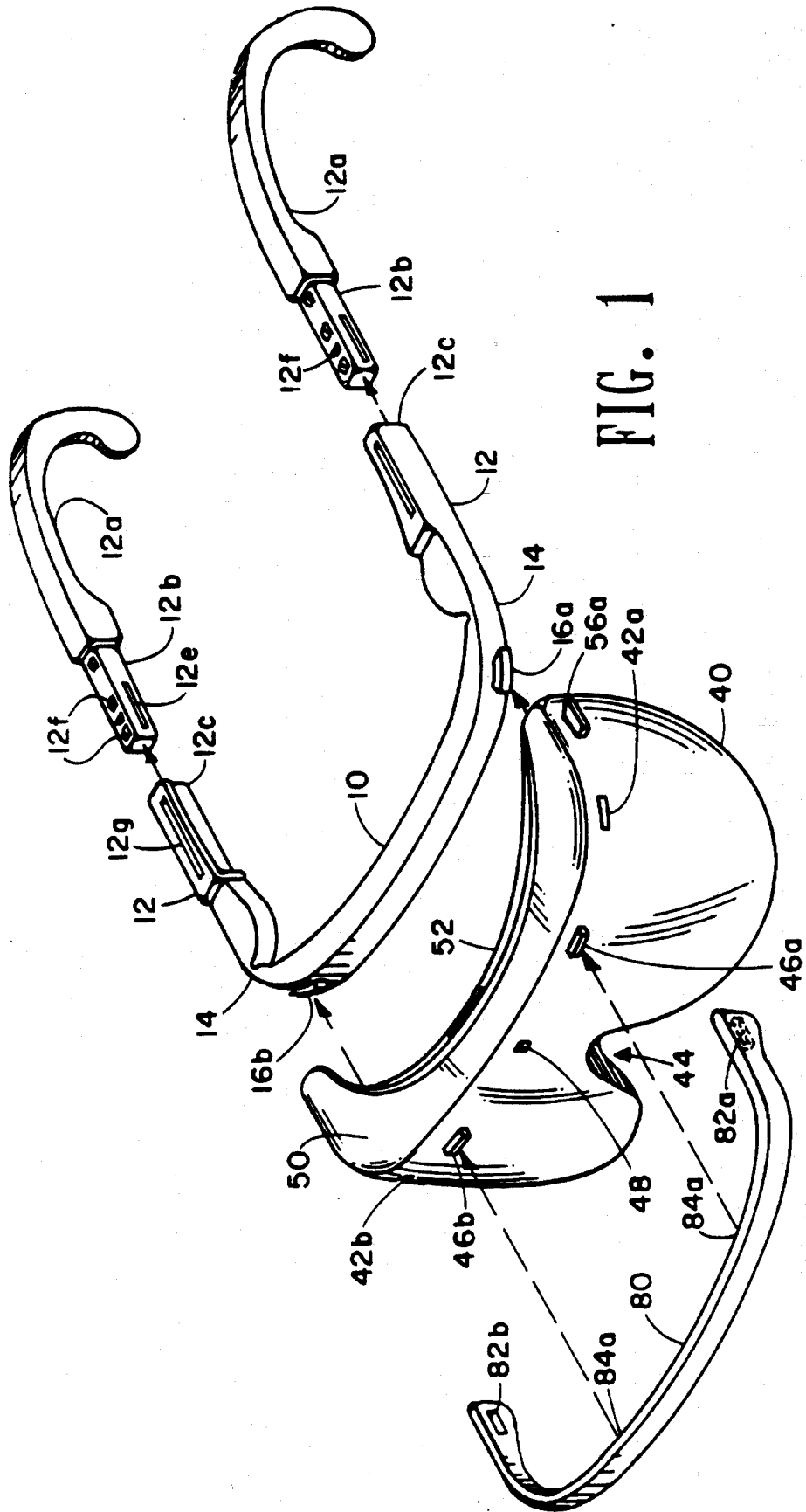
FIG. 1 is a perspective exploded view of a preferred embodiment of the spectacles of the present invention showing the brow bar, lens, and strip in position to be assembled.

An embodiment of the spectacles of this invention is shown in FIG. 1 exploded in a way to show how the parts of the lens fit together. Generally, the spectacles comprise a unitary brow bar 10, a unitary one piece lens 40, and a strip 80. The lens 40 may be formed with a reward facing channel along its upper edge overlying an inner side of the lens 40 into which the brow bar 10 may be received. To assemble, the bar 10 is sufficiently resilient to be flexed to allow the insertion of the tabs on the bar to be inserted into slows on the lens and snapped into the inner or wearer's side of the channel of lens 40 and the strip 80 is then snapped onto the outer side of the lens 40. The brow bar 10 is integrally molded to the temple pieces 12 through flexible plastic hinges 14 which allows the part to be molded in a single piece thus providing for the ease of assembly by the wearer. Toward either side of the brow bar 10 are tabs 16a and 16b which are configured to be inserted through corresponding slots 42a and 42b, respectively, on lens 40 which secures the lens 40 to the brow bar 10.

The preferred embodiment of FIG. 1 shows the temple pieces in their adjustable mode; i.e., as two pieces 12 and 12a. The rear piece 12a allows the size of the spectacles to be adjusted by the insertion of post 12b into sleeve 12c on the rearward facing temple piece 12 which is joined to brow bar 10 through hinge 14. As is better shown on FIG. 2, the post 12b is inserted into sleeve 12c with the nub 12d compresses slotted spring 12e allowing guide tabs 12f to enter the sleeve 12c and to enter and to move back and forth within guide slot 12g as the temple pieces 12a adjuster. The nubs 12d then may engage one of a series of ports 12h in the bottom of temple 12 appropriate to hold the temple pieces and the proper length for the wearer.

The lens 40 comprises a one piece ranged and curved front face piece adapted to wrap around the forehead to the wearers temples. The lens of the spectacles of the present invention are spherical in both the horizontal and vertical directions as more specifically described in U.S. Pat. No. 4,945,577, the disclosure of which is incorporated herein for all purposes. The lens 10 is supported on the nose of the wearer by a nose indentation bridge 44 which is preferably molded of thicker material to provide comfort for the wearer. The lens 40 may be molded of either clear or color tinted transparent or opaque plastic material and is substantially distortion free. Although tough transparent polycarbonate is the preferred molded plastic material, the lens 40 (and other spectacle materials) may be injection molded of the same or different suitable impact or fracture resistant material selected from a group consisting of polycarbonate, methyl methacrylate, cellulose propionate, cellulose acetate, and cellulose butyrate. If needed, the lens 40 may be tinted with color to reduce glare and/or coated with a layer of abrasion resistant material suitable to reduce scratching and scattering of light rays. Of course, the brow bar 10 is molded from a material which can be flexed to accommodate the molded flexible hinge and the flexing of the brow bar 10 in order to assemble the spectacles of this invention. The preferred material for this piece would be a tough flexible plastic material such as, for example, nylon, polyethylene, polypropylene, polyethylene/polyvinyl acetate copolymers and the like. Some polymers are better than others for this purpose and those skilled in the art will be able to make the proper selection. The molding of the bar and the hinge 14 is within the skill of the art.

The lens 40 also includes at least two tabs 46a and 46b along the upper part of the lens 40 for the purpose of carrying the stabilizer strip 80 which has a cosmetic and functional effect. At or near the horizontal center of the lens 40 is a port 48 for the purpose of inserting a pointed object to press against the brow bar 10 in order to dissemble the spectacles. The top of the lens 40 is bordered with a flange 50 leading back in the direction of the forehead of the wearer in order to provide some protection from foreign matter entering the eye area of the wearer from above. This flange 50 terminates against the brow of the wearer with an upwardly directing lip 52 which rests against the forehead of the wearer and, additionally forms the upper restraint of the channel, described later, into which the brow bar 10 is positioned during the assembly of the spectacles.

FIG. 3 shows a front view of the assembled spectacles, having lens 40 and nose bridge 44. The stabilizer strip 80 covers the slots 42a and 42b pawls 46a, 46b and port 48 to improve the appearance of the spectacles and to add greater stability to the protective eyewear. Lens 40 wraps around to the temples of the wearer thus providing eye safety from the side. At either end of the lens 40 adjacent the temple is a notch 56a and 56b integrally formed in the molded piece making up the lens 40. The stabilizer strip 80 terminates at either end by a slightly widened area carrying an indented hook 82a and 82b. When assembled, the hooks 82a and 82b are secured over the notches 56a and 56b of the lens and is positioned along the top of the outer face of lens 40 by indentations 84a and 84b which correspond to pawls 46a and 46b on the faces of the lens 40.

The assembled spectacles are illustrated by FIG. 4 which is a section taken through the nose notch 44 of the lens 40. It shows the brow bar 10 positioned in a channel formed in the molded lens piece 40 by the flange 50 and an inner flange 54, both of which extend substantially the entire width, along the top of the lens 40. The channel 54a is substantially the same width as the brow bar 10 in order to receive the brow bar when assembled. Also, shown in FIG. 4 as a part of the lower interior flange 54, is an upwardly facing lip 54b positioned to provide additional stabilizing effect to the brow bar 10 when the spectacles are assembled. To disassemble the spectacles, the stabilizing strip 80 is removed by snapping hooks 82a and 82b from notches 56a an 56b to reveal port 48 shown on FIG. 4. A pointed object such as an unfolded paper clip may be inserted through port 48 to push the center of brow bar 10 from channel 54a allowing disassembly to be effected. As an optional feature stabilizing strip 80 could include a lip 86 as shown on FIG. 4 to rest in a cutout 58 in lens 40. The strip 80 can be manufactured from a variety of materials which can be tinted with any one of a number colors to add greater adornment to the spectacles of this invention.

Figure 5A:
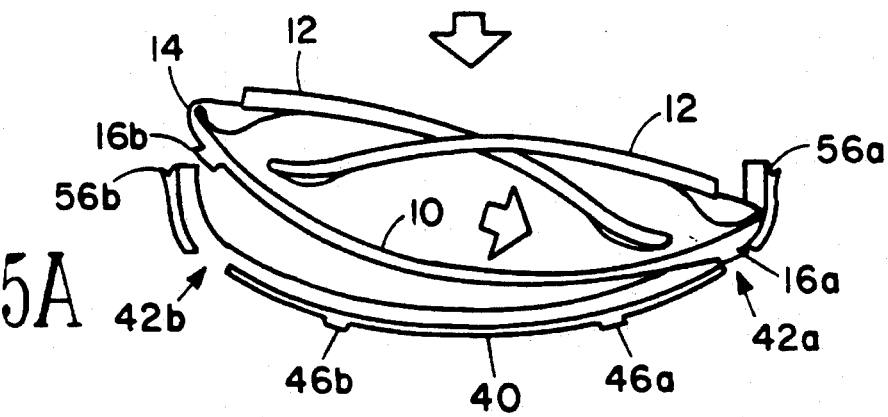
FIG. 5a is a top view of the preferred embodiment of the present invention showing a frame and a lens in which a frame hook is inserted into a matching lens slot to secure the lens to the frame brow piece.
Figure 5B:
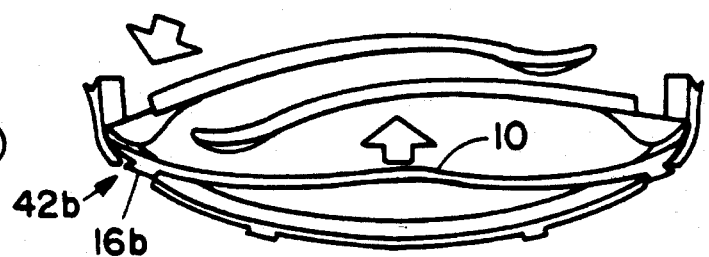
FIG. 5b is a top view of the preferred embodiment of the present invention in which the center of the frame is lifted and the other frame hook is inserted into the other matching lens slot.
Figure 5C:
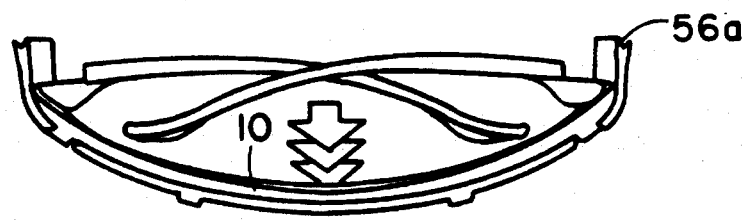
FIG. 5c is a top view of the preferred embodiment of the present invention showing the frame fully seated and latched into the lens.
Figure 5D:
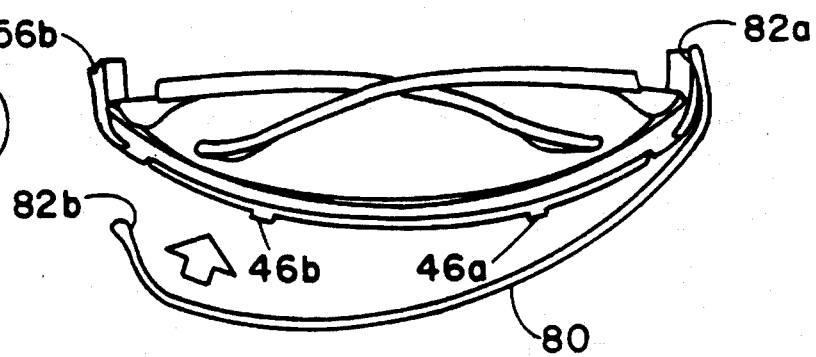
FIG. 5d is a top view showing the stabilizer strip snapped into position on one side preparatory to engaging the hook and notch to complete the assembly of the spectacles of this invention.

Referring now to FIGS. 5A through 5D there is shown the steps for the assembly of the spectacles of this invention which is one of the great advantages in that the pieces may be molded and then assembled by then the wearer at its convenience. It also allows the brow and stabilizing strip pieces to be kept when a lens becomes damaged or the wearer wishes to substitute a clear lens for a tinted lens. In addition, FIGS. 5A through 5D show an additional embodiment of this invention wherein the temples 12 are not adjustable but are molded in a single piece along with the brow bar 10 and the hinges 14. In FIG. 5A, with the arrows throughout showing the movement of parts, tab 16a is inserted into slot 42a of the lens 40. The brow bar 10 is flexed backwardly (FIB. 5B) and tab 16b inserted into slot 42b. The brow bar 10 is then flexed forwardly as shown in FIB. 5C where it slides into channel 54a (FIG. 4) which extends along the top, beneath flange 50, to hold the brow bar 10 along the top of the lens 40. In FIG. 5D the stabilizing strip 80, molded to conform to the shape of the outer face of the lens 40 is affixed by attaching hook 82a molded into the wide part of the end of the strip 80, to notch 56a molded into the end of the lens 40. Pawls 46a and 46b oriented along the top of lens 40 on the outer surface opposite the channel 56 extending across the inner surface of the lens 40, are covered by indentations, not shown, in the stabilizing strip 80 to orient the strip 80 substantially conforming to the orientation of channel 54a on the inside to snap securely into place by affixing hook 82b into notch 52b on the lens 40. The spectacles may be disassembled by reversing the order of assembly as set forth above.

From the description of the embodiments as set forth above and the affixed drawings, one skilled in the art could make many modifications and variations of the easily assembled protective eyewear set forth herein without departing from the spirit and scope of the instant invention.

What is claimed is:

1. Easily assembled protective eyewear, comprising:

a brow bar integrally connected on each end to temple pieces by formed flexible hinge strips which allows the temples to pivot between an open and collapsed position, said brow, temple pieces, and hinge strips integrally formed in a single molded piece;

a tab oriented on each end of the brow bar adjacent each hinge to securely hold a lens in position in front of the wearer's eyes;

a unitary lens having a nose bridge indentation and a slot positioned to receive each tab on the brow bar and at least two forwardly facing pawls along an upper edge of the lens with stabilizer notches at each side of the lens; and a stabilizer strip configured to conform to the shape of the forward face of the lens having indentations to receive each pawl and hooks at either end positioned to engage the stabilizing strip with the corresponding notch when assembled.

2. The protective eyewear of claim 1, wherein each temple piece is adjustable and includes a front end sleeve portion with a rearward facing opening and a telescoping rear end for engaging the head of the wearer which is adjustably attached into the sleeve portion with a post adapted to slidably fit into the sleeve and a means for holding the fit of the eyewear.

3. The protective eyewear of claim 1, wherein said lens is a spherically shaped lens adapted to wrap around the forehead of the wearer's temples.

4. Safety spectacles for providing eye protection comprising:

a one piece, spherical, wraparound lens formed with a rearwardly facing channel formed along the top of the lens by a pair of horizontal parallel, spaced-apart flanges disposed on an inner side of the top of said lens having slots through the lens on either side of the lens within the channel and a plurality of pawls on the outer face of the lens oriented along a line corresponding to the location of the channel; and an integrally molded unitary brow bar and a pair of collapsible temples molded together with a flexible plastic hinge which allows the temples to pivot between an open and collapsed position, wherein said brow bar includes a tab oriented to correspond to the slots through the lens and is sized to be received into the channel of said lens upon assembly.

5. The safety spectacles of claim 4 for providing eye protection wherein said lens also includes stabilizer notches on either side of the outer surface of the lens oriented in line with the tabs on the front of the lens; and a stabilizer strip configured to conform to the shape of the forward face of the lens having indentations to receive each pawl and further having hooks at either end positioned to engage the stabilizer notches when assembled.

6. The safety spectacles of claim 4 wherein the collapsible temples are adjustable and includes a sleeve portion attached to the flexible hinge on the front and is open to the rear; and an ear engaging piece with a forwardly directed post adapted to be received by the sleeve in a telescoping manner fitted with mating means to detachably secure the ear engaging piece to provide the desired fit of the spectacles.

\* \* \* \* \*